(12) United States Patent
Yamamoto et al.

(10) Patent No.: US 9,214,316 B2
(45) Date of Patent: Dec. 15, 2015

(54) COMPOSITE CHARGED PARTICLE BEAM APPARATUS

(71) Applicants: Yo Yamamoto, Chiba (JP); Xin Man, Chiba (JP); Tatsuya Asahata, Chiba (JP)

(72) Inventors: Yo Yamamoto, Chiba (JP); Xin Man, Chiba (JP); Tatsuya Asahata, Chiba (JP)

(73) Assignee: HITACHI HIGH-TECH SCIENCE CORPORATION (JP)

(*) Notice: Subject to any disclaimer, the term of this patent is extended or adjusted under 35 U.S.C. 154(b) by 0 days.

(21) Appl. No.: 13/622,023

(22) Filed: Sep. 18, 2012

(65) Prior Publication Data

US 2013/0082176 A1   Apr. 4, 2013

(30) Foreign Application Priority Data

Sep. 20, 2011  (JP) ................................. 2011-204508

(51) Int. Cl.
| | |
|---|---|
| *H01J 37/00* | (2006.01) |
| *H01J 37/22* | (2006.01) |
| *G01N 23/225* | (2006.01) |
| *H01J 37/30* | (2006.01) |
| *H01J 37/305* | (2006.01) |
| *G01N 23/04* | (2006.01) |

(52) U.S. Cl.
CPC ............... *H01J 37/222* (2013.01); *G01N 23/04* (2013.01); *G01N 23/225* (2013.01); *H01J 37/3005* (2013.01); *H01J 37/3056* (2013.01); *G01N 2223/045* (2013.01); *H01J 2237/31745* (2013.01)

(58) Field of Classification Search
CPC ............................... G01N 21/00; G01R 31/311
USPC ......................................................... 250/492.1
See application file for complete search history.

(56) References Cited

U.S. PATENT DOCUMENTS 6,664,552 B2 * 12/2003 Shichi et al. ............. 250/492.21
8,440,969 B2 *  5/2013 Moore et al. ................... 250/307
(Continued)

FOREIGN PATENT DOCUMENTS

JP          06231720         8/1994
JP         2001084951        3/2001
(Continued)

OTHER PUBLICATIONS

Notification of Reasons for Refusal mailed May 26, 2015 issued in Japanese Patent Appln. No. 2011-204508 together with English-language machine translation.

*Primary Examiner* — Phillip A Johnston
(74) *Attorney, Agent, or Firm* — Adams & Wilks

(57) ABSTRACT

A composite charged particle beam apparatus comprises an FIB column having an ion beam irradiation axis and an SEM column having an electron beam irradiation axis, the FIB and SEM columns being arranged relative to one another so that the beam irradition axes intersect with each other substantially at a right angle. A sample stage is provided for mounting a sample, and a detector detects secondary particles generated from the sample when irradiated with the ion beam or the electron beam. An observation image formation portion forms an FIB image and an SEM image based on a detection signal of the detector. A display portion displays the FIB image and the SEM image in which a horizontal direction of the sample in the FIB image and said horizontal direction of the sample in the SEM image are the same thereby making it possible for an operator to easily comprehend the positional relationship of the observation image of the sample.

6 Claims, 5 Drawing Sheets

(56) References Cited

U.S. PATENT DOCUMENTS

2008/0265158 A1* 10/2008 Iwasaki .................. 250/310
2009/0020698 A1* 1/2009 Muto et al. .............. 250/310

FOREIGN PATENT DOCUMENTS

JP          2007018935      1/2007
JP          2011198581     10/2011

* cited by examiner (a)

(b)

(a)

(b)

(c)

(a)

(b)

(a)

(b)

COMPOSITE CHARGED PARTICLE BEAM APPARATUS

BACKGROUND OF THE INVENTION

1. Field of the Invention

The present invention relates to a charged particle beam apparatus, such as a focused ion beam apparatus and a scanning electron microscope.

2. Description of the Related Art

A focused ion beam (FIB) apparatus is known as an apparatus for processing and observing a minute sample such as a semiconductor device. Further, an FIB-SEM composite apparatus is known as an apparatus for observing a sample under processing by a focused ion beam in real time through a scanning electron microscope (SEM).

In general, in the FIB-SEM composite apparatus, an FIB column and an SEM column are arranged so that an irradiation axis of the FIB column and an irradiation axis of the SEM column may form an angle of about 50° to 60° therebetween. With this arrangement, the same region of the sample can be observed by the FIB and the SEM. The FIB-SEM composite apparatus displays an observation image so that the same observation target may be displayed in an FIB image and an SEM image while having the same perpendicular direction.

For example, as illustrated in FIG. 5A, the FIB-SEM composite apparatus irradiates a lamellar sample 24 fixed on a sample holder 23 with an ion beam 51 and an electron beam 52, to thereby acquire observation images. An SEM image 55 on the left of FIG. 5B and an FIB image 56 on the right of FIG. 5B are the acquired observation images. The SEM image 55 and the FIB image 56 are displayed so that an observation plane 24a of the lamellar sample 24 has the same perpendicular direction. Accordingly, the positional relationship of the lamellar sample 24 observed through the SEM image 55 and the FIB image 56 is made clear, and it is therefore easy for an operator to operate.

By the way, along with the reduction in device dimensions in recent years, it is requested to perform high-resolution SEM observation on a sample surface processed by the FIB. Then, a composite charged particle beam apparatus in which an FIB column and an SEM column are orthogonally arranged is proposed (see Japanese Patent Application Laid-open No. 6-231720).

This apparatus can perform SEM observation on a cross-section processed by the FIB from the perpendicular direction. In general, the SEM can observe an observation plane from the perpendicular direction at a high resolution. Therefore, with the apparatus of Japanese Patent Application Laid-open No. 6-231720, the cross-section processed by the FIB can be observed by the SEM in-situ at a high resolution.

However, in the apparatus of Japanese Patent Application Laid-open No. 6-231720, the FIB column and the SEM column are orthogonally arranged, and hence the sample surface observed by the FIB cannot be observed by the SEM. Therefore, there has been a problem in that it is difficult for the operator to grasp the positional relationship of the sample in an observation image.

SUMMARY OF THE INVENTION

The present invention has been made in view of the above-mentioned circumstances, and provides a composite charged particle beam apparatus in which an FIB column and an SEM column are orthogonally arranged and which enables an operator to easily grasp a positional relationship of a sample observed through an FIB image and an SEM image.

In order to achieve the above-mentioned object, the present invention provides the following measures.

There is provided a composite charged particle beam apparatus, including: an FIB column; an SEM column, which is arranged substantially at a right angle with respect to the FIB column; a sample stage for mounting a sample; a detector for detecting a secondary particle generated from the sample; an observation image formation portion for forming an FIB image and an SEM image based on a detection signal of the detector; and a display portion for displaying the FIB image and the SEM image in which a horizontal direction of the sample in the FIB image and a horizontal direction of the sample in the SEM image are the same.

The composite charged particle beam apparatus further includes a scanning control portion for controlling beam scanning directions of the FIB column and the SEM column so that the horizontal direction of the sample in the FIB image and the horizontal direction of the sample in the SEM image become the same.

The composite charged particle beam apparatus further includes an image processing portion for performing image processing on one of the FIB image and the SEM image so that the horizontal direction of the sample in the FIB image and the horizontal direction of the sample in the SEM image become the same.

The composite charged particle beam apparatus further includes a three-dimensional image formation portion for reversing horizontal directions of a plurality of the SEM images, which are acquired by repeating observation plane formation by FIB irradiation and SEM image acquisition of the observation plane, and for forming a three-dimensional image from the reversed plurality of the SEM images.

According to the composite charged particle beam apparatus of the present invention, the FIB image and the SEM image having the same horizontal direction are displayed, and hence the positional relationship of the sample observed through the FIB image and the SEM image can be made clear, thus enabling the operator to operate easily.

DETAILED DESCRIPTION OF THE PREFERRED EMBODIMENTS

In an embodiment of the present invention, in an apparatus including an FIB column and an SEM column which are orthogonally arranged, the display directions of an FIB image and an SEM image are aligned.

A conventional composite apparatus in which the FIB column and the SEM column are arranged at about 50° to 60°, the same observation plane can be observed, and hence the same target can be displayed in an FIB image and an SEM image. Therefore, regardless of the display direction, an operator can clearly grasp the positional relationship of a sample.

However, in the apparatus in which the FIB column and the SEM column are orthogonally arranged, particularly in the case where an observation plane formed by an ion beam is irradiated with an electron beam from a direction substantially perpendicular to the observation plane to acquire an SEM image of the observation plane in-situ without moving the sample, the observation plane cannot be displayed in an FIB image.

In addition, even when the FIB image and the SEM image having the same perpendicular direction are displayed as in the conventional apparatus, if the same target cannot be displayed in the FIB image and the SEM image, the operator cannot easily grasp the positional relationship of the sample.

In light of the above, in the embodiment of the present invention, the horizontal display directions of the FIB image and the SEM image are aligned. With this, even when the same target cannot be displayed in the FIB image and the SEM image, the display directions are aligned, and hence it is easy to intuitively grasp the positional relationship of the sample from the FIB image and the SEM image.

In addition, in the case of constructing a three-dimensional image from acquired SEM images, by additionally reversing the horizontal direction of the acquired SEM image, it is possible to construct a three-dimensional image which reproduces the actual positional relationship of the sample.

Now, a composite charged particle beam apparatus according to the embodiment of the present invention is described.

Figure 1:
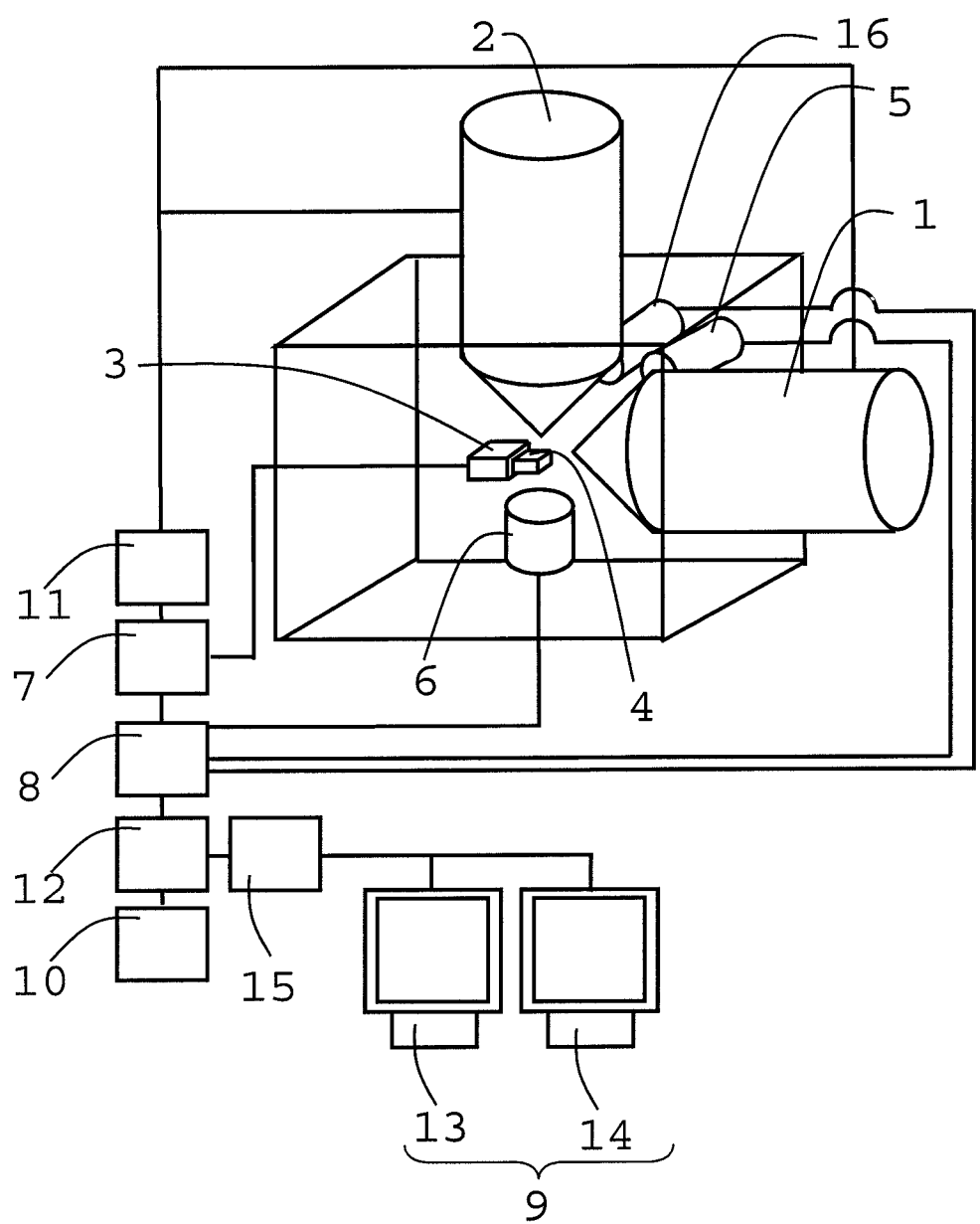
FIG. 1 is a configuration diagram of a composite charged particle beam apparatus according to an embodiment of the present invention.

As illustrated in FIG. 1, the composite charged particle beam apparatus of this embodiment includes an FIB column 1, an SEM column 2, a sample stage 3, a secondary electron detector 5, and a transmission electron detector 6. The FIB column 1 and the SEM column 2 are arranged so that beam irradiation axes thereof may intersect with each other substantially perpendicularly, and that the beam irradiation axes may intersect with each other in the vicinity of a sample 4 fixed on the sample stage 3. With this configuration, a processed surface which has been processed by an ion beam radiated from the FIB column 1 can be irradiated with an electron beam from the SEM column 2 substantially perpendicularly, thus enabling SEM observation.

The sample stage 3 is driven by a stage drive mechanism 7. The sample stage 3 includes a rotation mechanism which is capable of rotating about a beam irradiation axis of the FIB column 1, and a movement mechanism which is capable of moving in three-axis directions of X, Y, and Z. The sample stage 3 further includes a tilt mechanism for tilting the sample 4 with respect to the ion beam. In this way, the sample 4 can be irradiated with the ion beam from a desired angle, to thereby process the sample 4.

The transmission electron detector 6 is arranged on a beam irradiation axis of the SEM column 2. The transmission electron detector 6 can detect electrons that have transmitted through the sample 4 or electrons that have been scattered by the sample 4 when the electron beam is radiated from the SEM column 2.

The secondary electron detector 5 and the transmission electron detector 6 are connected to an image formation portion 8. The image formation portion 8 forms an FIB image and an SEM image based on a detection signal of the secondary electron detector 5. In addition to the secondary electron detector 5, the composite charged particle beam apparatus includes a reflected electrode detector inside the electron beam column 2, and hence a reflected electron image can also be formed. The composite charged particle beam apparatus further includes a screen for detecting scattered electrons which are emitted from the sample 4, and hence an EBSD image can also be formed. The image formation portion 8 forms a transmission electron image based on a detection signal of the transmission electron detector 6. The composite charged particle beam apparatus further includes an EDS detector 16 for detecting X-rays which are emitted from the sample 4.

A display portion 9 displays the FIB image, the SEM image, and the transmission electron image. The display portion 9 includes a display device 13 and a display device 14, and hence the respective observation images can be displayed on different display devices. The respective observation images can also be displayed on one display device. In this case, the display portion 9 includes a single display device.

An operator operates the composite charged particle beam apparatus via an input portion 10. The operator can input beam irradiation conditions, setting of a processing region, and the like.

A beam scanning control portion 11 controls scanning directions of the ion beam and the electron beam radiated from the FIB column 1 and the SEM column 2.

An image processing portion 12 performs image processing on the observation image such as the FIB image and the SEM image formed by the image formation portion 8.

The composite charged particle beam apparatus further includes a three-dimensional image formation portion 15 for forming a three-dimensional image from a plurality of SEM images formed by the image formation portion 8.

First Embodiment

Figure 2:
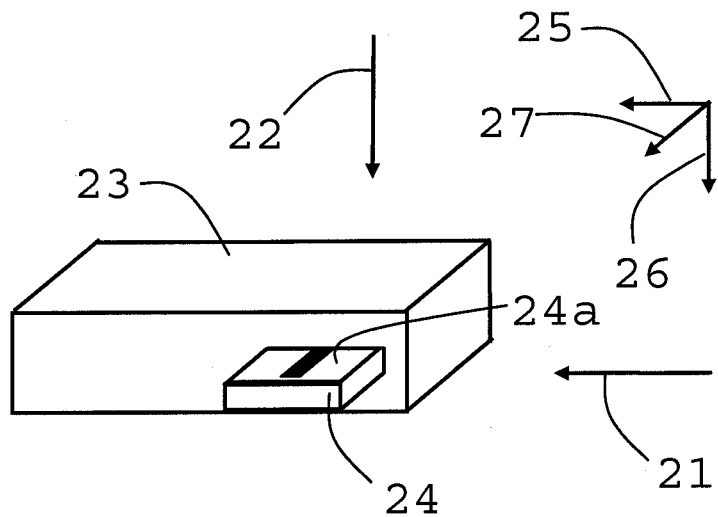
FIGS. 2A to 2B are diagrams illustrating sample observation according to the embodiment of the present invention.
Figure 2:
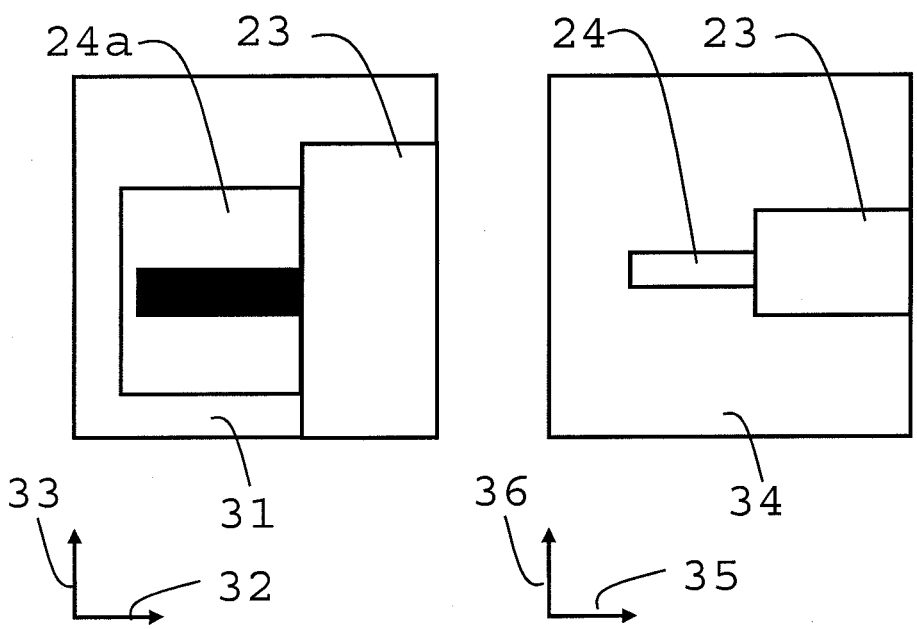

A first embodiment of the present invention of displaying an observation image of a sample is described. FIG. 2A is a diagram illustrating irradiation directions of an ion beam 21 and an electron beam 22 with respect to a lamellar sample 24 in the above-mentioned composite charged particle beam apparatus.

The lamellar sample 24 is fixed to a sample holder 23. The composite charged particle beam apparatus irradiates the lamellar sample 24 on an observation plane 24a side with the ion beam 21 so that the lamellar sample 24 is thinned, to thereby perform thinning processing. The observation plane 24a is irradiated with the ion beam 21 from a direction substantially parallel to the observation plane 24a. An FIB image 34 on the right of FIG. 2B is an observation image which is acquired by radiating and scanning the ion beam from this direction.

The composite charged particle beam apparatus observes the observation plane 24a by the SEM during processing of the lamella or before and after processing of the lamella. The composite charged particle beam apparatus irradiates the observation plane 24a with the electron beam 22 from a direction substantially perpendicular to the observation plane 24a. A high-resolution observation image can be acquired by irradiating the observation plane with the electron beam from the direction substantially perpendicular to the observation plane. An SEM image 31 on the left of FIG. 2B is an observation image which is acquired by radiating and scanning the electron beam 22 from this direction.

Next, the setting of a display direction of the observation image is described. Regarding a coordinate system of the lamellar sample 24, the ion beam irradiation direction is set as an X-axis direction 25, the electron beam irradiation direction is set as a Y-axis direction 26, and the direction of the Z axis is set as a Z-axis direction 27.

The FIB image 34 is displayed so that an X-axis direction 35 of the FIB image may be aligned with the direction opposite to the Z-axis direction 27 of the coordinate system of the lamellar sample 24, and that a Y-axis direction 36 of the FIB image may be aligned with the Y-axis direction 26 of the coordinate system of the sample 24.

The SEM image 31 is displayed so that an X-axis direction 32 of the SEM image may be aligned with the Z-axis direction 27 of the coordinate system of the sample 24, and that a Y-axis direction 33 of the SEM image may be aligned with the direction opposite to the X-axis direction 25 of the coordinate system of the lamellar sample 24.

Figure 5:
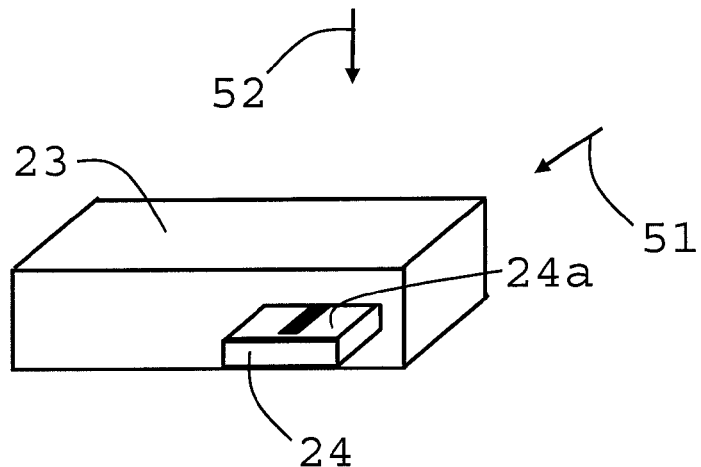
FIGS. 5A and 5B are diagrams illustrating sample observation performed by a conventional FIB-SEM composite apparatus.
Figure 5:
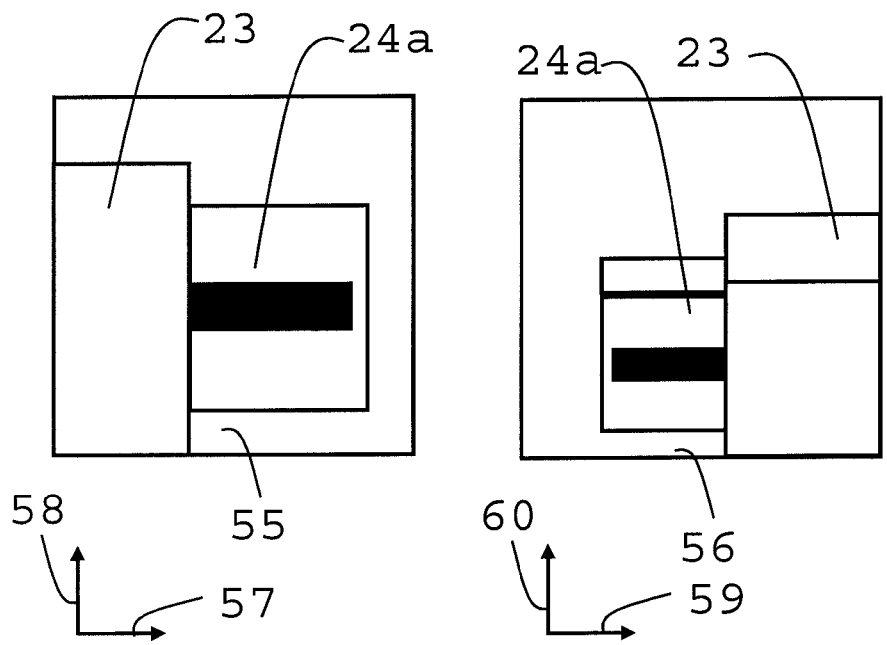

In the conventional FIB-SEM composite apparatus, as illustrated in FIG. 5B, an X-axis direction 57 of an SEM image is the direction opposite to an X-axis direction 59 of an FIB image. On the other hand, in the composite charged particle beam apparatus, as illustrated in FIG. 2B, the X-axis direction 32 of the SEM image and the X-axis direction 35 of the FIB image are displayed in the same direction. With this, even in the SEM image 31 and the FIB image 34 which cannot display the same observation plane, the X-axis directions thereof are aligned, and hence the operator can easily grasp the positional relationship of the sample 24.

Second Embodiment

Figure 3:
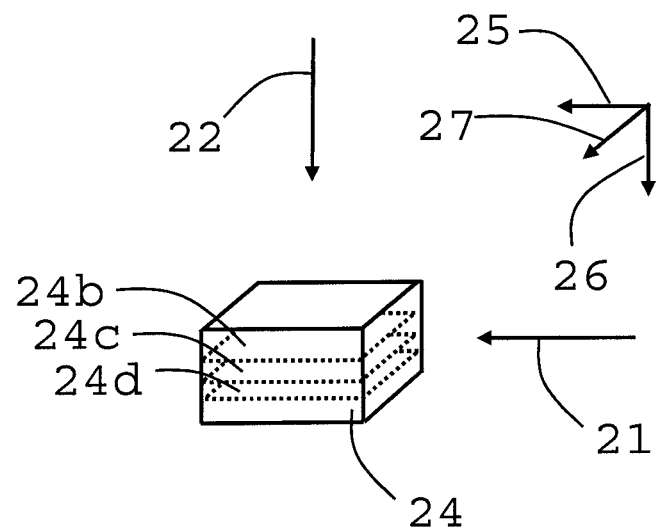
FIGS. 3A to 3C are diagrams illustrating three-dimensional image formation according to another embodiment of the present invention.
Figure 3:
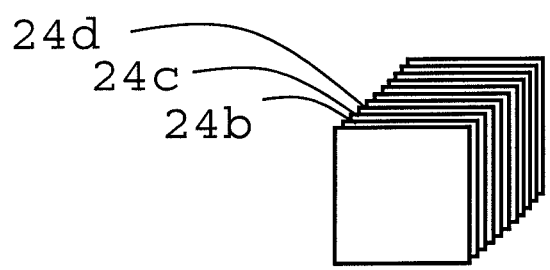
Figure 3:
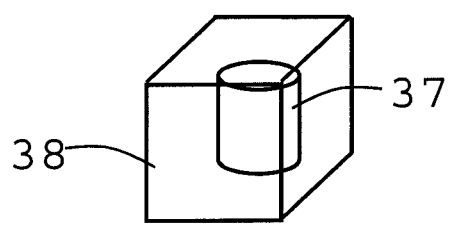

A second embodiment of the present invention of constructing a three-dimensional image is described. As illustrated in FIG. 3A, the composite charged particle beam apparatus performs slice processing on the sample 24 by the ion beam 21, and observes an exposed surface by the SEM. Based on SEM images having sliced surfaces and an interval between a sliced surface and the next sliced surface, the composite charged particle beam apparatus arranges the SEM images at an interval corresponding to the slicing interval of the SEM images, to thereby construct a three-dimensional image.

The composite charged particle beam apparatus scans the ion beam 21 to irradiate the sample 24 with the ion beam 21 in parallel to the Z-axis direction 27 of the coordinate system of the sample 24, to thereby process the sample 24. The composite charged particle beam apparatus irradiates a sliced surface 24b, which is exposed by the processing, with the electron beam 22 from a direction substantially perpendicular to the sliced surface 24b, to thereby acquire and store an SEM image. The composite charged particle beam apparatus performs processing by the ion beam 21 again to expose a sliced surface 24c, and acquires an SEM image of the sliced surface 24c. Next, in order to expose a sliced surface 24d, the composite charged particle beam apparatus repeats the slice processing and the SEM image acquisition.

The processing and observation can be performed without changing the incident directions of the ion beam 21 and the electron beam 22, and hence the composite charged particle beam apparatus can acquire a high-resolution SEM image efficiently.

Next, processing performed by the three-dimensional image formation portion 15 is described. The composite charged particle beam apparatus arranges the stored SEM images of the sliced surfaces so as to reproduce the structure of the lamellar sample 24 as illustrated in FIG. 3B. With this, the composite charged particle beam apparatus can form a three-dimensional image 38 of the lamellar sample 24 as illustrated in FIG. 3C. The three-dimensional image 38 can reproduce the shape of a structure 37 inside the lamellar sample 24, and hence the composite charged particle beam apparatus can easily grasp such a structure that is difficult to grasp from a two-dimensional image.

Further, the three-dimensional image formation portion 15 performs processing of aligning the direction of the acquired SEM image and the actual direction of an observation target.

Figure 4:
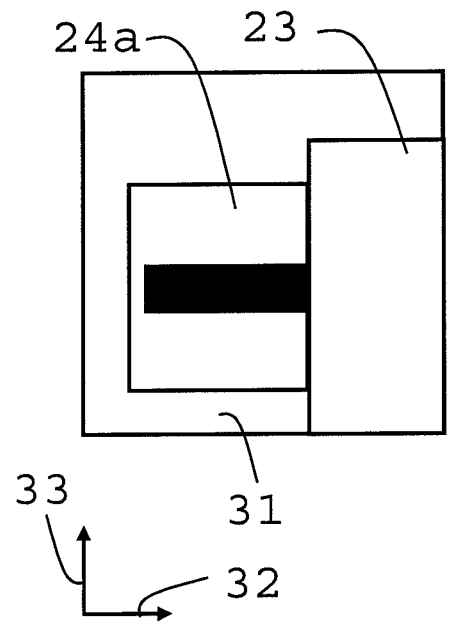
FIGS. 4A and 4B are diagrams illustrating the three-dimensional image formation according to the another embodiment of the present invention.
Figure 4:
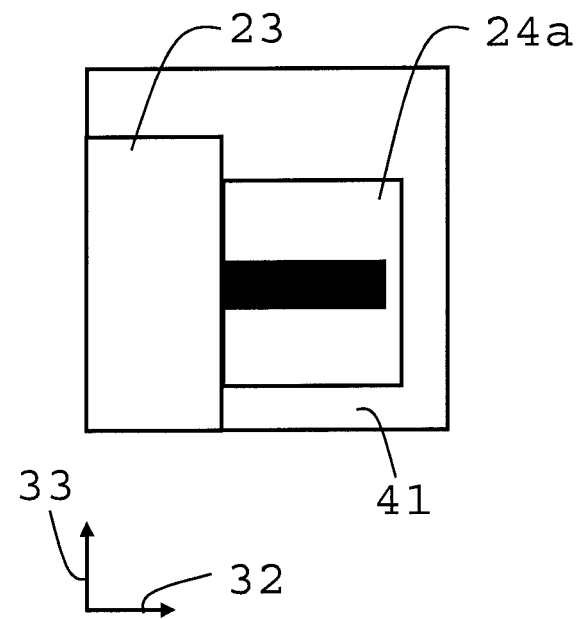

FIG. 4A is an acquired SEM image 31. An X-axis direction 32 of the SEM image is opposite to that of the actual lamellar sample 24. Then, the composite charged particle beam apparatus reverses the SEM image 31 so as to reverse the X-axis direction as illustrated in FIG. 4B. By forming a three-dimensional image with the use of a reversed SEM image 41, the composite charged particle beam apparatus can form a three-dimensional image which also reproduces the actual direction of the lamellar sample 24.

The above description is about an SEM image, but the composite charged particle beam apparatus may use a transmission electron image, a reflected electron image, an EDS image, and an EBSD image instead of using an SEM image.

What is claimed is:

1. A composite charged particle beam apparatus, comprising:
   an FIB column having an ion beam irradiation axis;
   an SEM column having an electron beam irradiation axis, the SEM column being arranged relative to the FIB column so that the beam irradiation axes thereof intersect with each other substantially at a right angle;
   a sample stage for mounting a sample;
   a detector for detecting secondary particles generated from the sample;
   an observation image formation portion for forming an FIB image and an SEM image based on a detection signal of the detector; and
   a display portion for displaying the FIB image and the SEM image such that the horizontal display direction of the sample is the same in both the FIB image and the SEM image.

2. A composite charged particle beam apparatus according to claim 1, further comprising a scanning control portion for controlling beam scanning directions of the FIB column and the SEM column so that the horizontal display direction of the sample in the FIB image and the horizontal display direction of the sample in the SEM image become the same.

3. A composite charged particle beam apparatus according to claim 1, further comprising an image processing portion for performing image processing on one of the FIB image and the SEM image so that the horizontal display direction of the sample in the FIB image and the horizontal display direction of the sample in the SEM image become the same.

4. A composite charged particle beam apparatus according to claim 3, further comprising a three-dimensional image formation portion for reversing horizontal directions of a plurality of the SEM images, which are acquired by repeating observation plane formation by FIB irradiation and SEM image acquisition of the observation plane, and for forming a three-dimensional image from the reversed plurality of the SEM images.

5. A composite charged particle beam apparatus according to claim 2, further comprising a three-dimensional image formation portion for reversing horizontal directions of a plurality of the SEM images, which are acquired by repeating observation plane formation by FIB irradiation and SEM image acquisition of the observation plane, and for forming a three-dimensional image from the reversed plurality of the SEM images.

6. A composite charged particle beam apparatus according to claim 1, further comprising a three-dimensional image formation portion for reversing horizontal directions of a plurality of the SEM images, which are acquired by repeating observation plane formation by FIB irradiation and SEM image acquisition of the observation plane, and for forming a three-dimensional image from the reversed plurality of the SEM images.

\* \* \* \* \*